US008979781B2

(12) United States Patent
Cook et al.

(10) Patent No.: US 8,979,781 B2
(45) Date of Patent: Mar. 17, 2015

(54) EMT SPLINT (76) Inventors: Martin Joseph Cook, Smithtown, NY (US); Martin Raymond Cook, Floral Park, NY (US)

(*) Notice: Subject to any disclaimer, the term of this patent is extended or adjusted under 35 U.S.C. 154(b) by 299 days.

(21) Appl. No.: 13/558,717

(22) Filed: Jul. 26, 2012

(65) Prior Publication Data
US 2014/0031732 A1 Jan. 30, 2014

(51) Int. Cl.
*A61F 5/00* (2006.01)
(52) U.S. Cl.
USPC .................................. 602/16; 602/5
(58) Field of Classification Search
USPC ............ 128/869, 879, 880–882, 846; 602/16, 602/23, 26–29, 5, 870, 877, 878
See application file for complete search history.

(56) References Cited

U.S. PATENT DOCUMENTS

| | | | |
|---|---|---|---|
| 3,921,231 A * | 11/1975 | Bourgraf et al. ................ 5/627 |
| 4,174,709 A | 11/1979 | Maddux | |
| 4,241,731 A * | 12/1980 | Pauley ............................... 602/4 |
| 4,280,490 A * | 7/1981 | Santy ............................... 602/16 |
| 4,299,210 A * | 11/1981 | Santy ............................... 602/19 |
| 4,807,609 A * | 2/1989 | Meals ............................. 602/20 |
| 5,063,919 A | 11/1991 | Silverberg | |
| 5,658,241 A | 8/1997 | Deharde et al. | |
| 5,749,840 A | 5/1998 | Mitchell et al. | |
| 5,803,087 A * | 9/1998 | Thompson .................... 128/870 |
| 6,042,557 A | 3/2000 | Ferguson et al. | |
| 6,179,798 B1 | 1/2001 | Nelson | |
| 6,293,918 B1 | 9/2001 | Wang | |
| 6,398,748 B1 | 6/2002 | Wilson | |
| 6,478,758 B1 | 11/2002 | Hassler | |
| 6,533,741 B1 * | 3/2003 | Lee et al. ......................... 602/20 |
| 6,669,659 B2 | 12/2003 | Dittmer et al. | |
| 6,936,020 B2 | 8/2005 | Davis | |
| 7,662,117 B2 | 2/2010 | Parizot | |
| 7,670,308 B2 | 3/2010 | Borschneck | |
| 2010/0170036 A1 * | 7/2010 | Shirandami .................. 5/81.1 R |

* cited by examiner

*Primary Examiner* — Kim M Lewis
(74) *Attorney, Agent, or Firm* — Sorell, Lenna & Schmidt, LLP (57) ABSTRACT A splint system includes a first base member including at least one connector portion. A second base member including at least one connector portion having a cavity, wherein an interior surface of the cavity includes slidable portions and coupling portions, the first and second base members being aligned to form a longitudinal passage. A shaft member is disposed in the longitudinal passage, and when the coupling portions of the shaft member align with the coupling portions of the second base member, the first and second base members are fixed relative to each other.

20 Claims, 12 Drawing Sheets

EMT SPLINT

TECHNICAL FIELD

The present disclosure generally relates to orthopedic splints, and more particularly to a splint device for providing quick and secure support for a limb or digit.

BACKGROUND

Splints or braces are typically used to hold portions of a limb, such as wrist or elbow joints, in a desired position to promote healing of bone or other tissue and/or prevent further injury. In the instance of traumatic injuries, splints are often used by emergency medical technicians and paramedics to immobilize an injured area to prevent further damage during transportation. The injured area must be quickly immobilized and moreover, movement of the injured area must be prevented to avoid further damage.

Both physical therapy and surgical alternatives frequently include the use of some form of orthopedic splint. Such orthopedic splints are available as adjustable "off-the-shelf" devices or hand crafted custom orthotics molded to fit the individual patient or specific application.

The degree of flexion or extension of a joint, or angle which is needed to be maintained, may vary from patient to patient depending on the location and type of injury or on the progress of the patient's therapy. However, the angle at which most splints hold the joint has generally not been easily adjustable. While some mechanisms exist for adjusting the position of a splint, they often require installing and manipulating hardware such as machine screws or bolts and wing nuts at medial and lateral sides of the splint. Using such complex mechanisms can waste valuable time in the event where a traumatic injury must be immediately immobilized. Thus, there remains a need for improvement of such a splint to provide an easier mechanism for selecting and securing the angle of flexion of the splint.

SUMMARY

Accordingly, a splint device and method for immobilizing an area is provided. In one embodiment, in accordance with the principles of the present disclosure, a splint device is provided. The device comprises a splint system comprising a first base member including at least one connector portion having a cavity, wherein an interior surface of the cavity includes coupling portions; a second base member forming a hinged connection with the first base member, each of the first and second base members including at least one surface for contacting a body region, the second base member including at least one connector portion having a cavity, wherein an interior surface of the cavity includes slidable portions and coupling portions, and wherein the first and second base members are aligned so that each cavity of their respective at least one connector portions form a longitudinal passage; and a shaft member disposed in said longitudinal passage, wherein a surface of the shaft member includes slidable portions and coupling portions alternating along a longitudinal direction of the shaft member, such that when the slidable portions of the shaft member align with the coupling portions of the second base member, the first and second base members are angularly adjustable, and when the coupling portions of the shaft member align with the coupling portions of the second base member, the first and second base members are fixed relative to each other.

In one embodiment, the device comprises a splint system comprising a first base member including two connector portions having a cylindrical cavity, wherein an interior surface of the cylindrical cavity includes slidable portions and coupling portions in an alternating arrangement along a longitudinal direction of the first base member; a second base member including two connector portions having a cylindrical cavity, wherein an interior surface of the cylindrical cavity includes slidable portions and coupling portions in an alternating arrangement along a longitudinal direction of the first base member, and wherein the first and second base members are aligned so that each cylindrical cavity of their respective two connector portions form a longitudinal passage; and a shaft member inserted into said longitudinal passage, wherein a surface of the shaft member includes slidable portions and coupling portions in an alternating arrangement along a longitudinal direction of the shaft member, wherein the shaft is fully insertable within the longitudinal passage to provide a locked position in which the coupling portions of the shaft member are engaged with the coupling portions of the first and second base members to fix a position of the first member relative to the second member, and wherein the shaft is configured to be partially removable from the longitudinal passage to provide an adjustable position in which the slidable portions of the shaft member are oriented within the coupling portions of the second base member to enable pivotal movement of the second base member relative to the shaft member.

In one embodiment, a method for immobilizing an area of the body is provided, the method comprising the steps of: accessing an area of the body desired to be immobilized; providing a first base member including at least one connector portion having a cavity, wherein an interior surface of the cavity includes coupling portions, a second base member including at least one connector portion having a cavity, wherein an interior surface of the cavity includes slidable and coupling portions, and wherein the first and second base members are aligned so that each cavity of their respective at least one connector portions form a longitudinal passage, and a shaft member inserted into said longitudinal passage, wherein a surface of the shaft member includes slidable and coupling portions; adjusting the shaft member to an adjustable position and placing the first and second base members on the area of the body; pivoting at least one of the base members to a desired position; and adjusting the shaft member to a locked position to immobilize the area of the body by fixing the position of the first member relative to the second member.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of the splint device and related methods of use disclosed are discussed in terms of medical devices for the treatment and immobilization of areas of a patient, and more particularly, in terms of a splint device and method for immobilizing injured areas, such as joints and other flexible areas of the body. It is envisioned that the splint device and method may be employed in emergency applications such as immobilization of injured areas in the event of traumatic injury. The splint device and method may be used with additional devices and methods for further treating the area to be immobilized.

It is contemplated that one or all of the components of the splint system may be disposable, peel-pack, pre-packed sterile devices. One or all of the components of the splint system may be reusable. The splint system may be configured as a kit with multiple sized and configured components.

It is envisioned that the present disclosure may be employed to treat and immobilize areas of the body such as, for example, knees, elbows, ankles, digits, and other body regions, in particular, jointed areas. It is contemplated that the present disclosure may be employed for treatment of traumatic injuries needing immediate immobilization and/or with other joint related applications, including those associated with diagnostics and therapeutics. It is further contemplated that the disclosed splint system and methods may be alternatively employed in rehabilitative treatment and physical therapy with a patient to adjustably support areas of the body during recovery and healing. The present disclosure may also be alternatively employed with procedures for treating the body regions. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a splint system and related methods of employing the splint system in accordance with the principles of the present disclosure. Alternate embodiments are also disclosed. Reference will now be made in detail to the exemplary embodiments of the present disclosure, which are illustrated in the accompanying figures. Turning now to FIGS. 1-12, there is illustrated components of a splint system, such as, for example, a splint system 100, 200 in accordance with the principles of the present disclosure.

The components of a splint system 100 can be fabricated from any substantially rigid and/or flexible materials suitable for medical applications, including metals, synthetic polymers, ceramics, wood and/or their composites and combinations thereof, depending on the particular application and/or preference of a medical practitioner. For example, the components of splint system 100, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), aluminum, ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene and epoxy. Various components of splint systems 100, 200 may have material composites, including the above materials, to achieve various desired characteristics such as strength, rigidity, resiliency, elasticity, compliance, biomechanical performance, durability and radiolucency or imaging preference. The components of splint system 100, 200, individually or collectively, may also be fabricated from a heterogeneous material such as a combination of two or more of the above-described materials. The components of splint system 100, 200 may each be monolithically formed and integrally connected, and may further include fastening elements, locking or securing mechanisms and/or toggle mechanisms as described herein.

Figure 1:
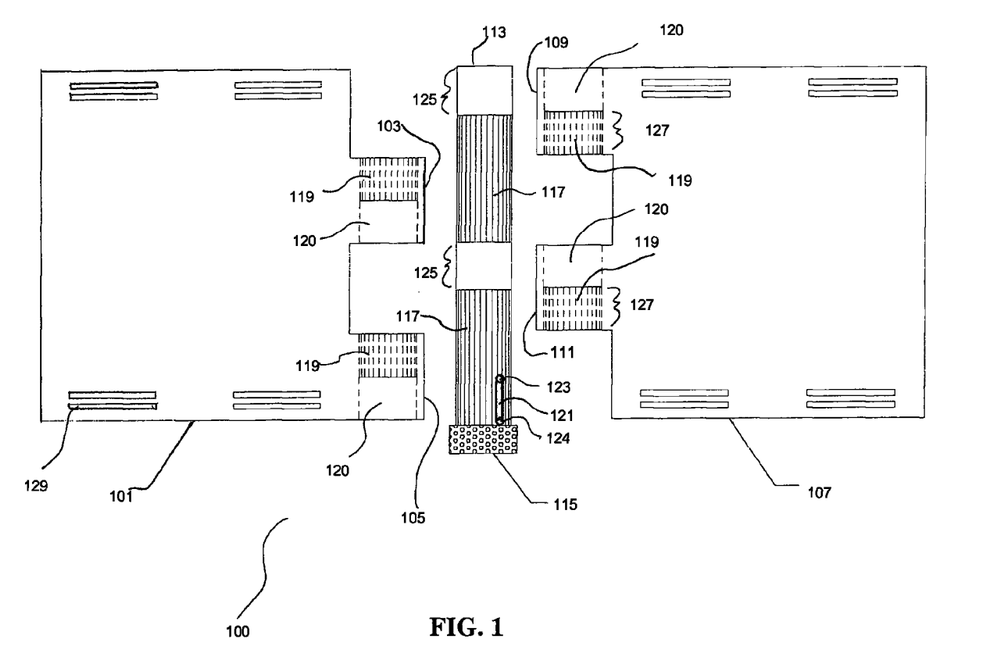
FIG. 1 is a front exploded view of one embodiment of separate components of a splint device in accordance with the principles of the present disclosure.
Figure 11:
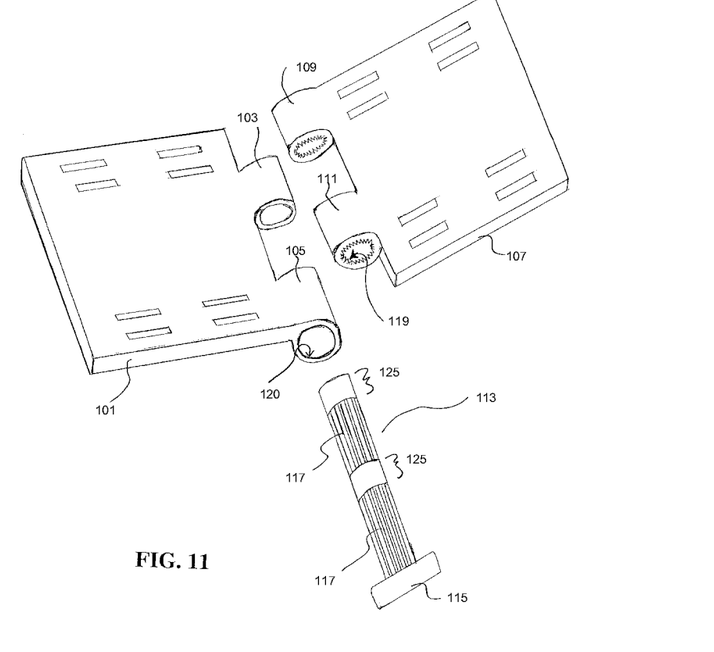
FIG. 11 is a perspective view of one embodiment of separate components of a splint device in accordance with the principles of the present disclosure.

FIG. 1 illustrates a front exploded view of one embodiment of separate components of a splint device 100 in accordance with the principles of the present disclosure, in which interior views of connector portions 103, 105, 109, 111 are provided for sake of clarity. FIG. 11 is a perspective view of one embodiment of separate components of a splint device in accordance with the principles of the present disclosure.

In one embodiment, the splint system 100 comprises a first substantially rigid base member 101 and a second substantially rigid base member 107, which each includes at least one surface configured for contacting and supporting a body region, such as a limb or digit. The first and second members 101, 107 may be any shape, such as, for example, oval, oblong, triangular, rectangular, square, polygonal, irregular, uniform, non-uniform, variable and/or tapered, and may be any thickness, length or width and/or may be further adapted to conform to a particular body area or shape.

Each of the first and second base members 101, 107 may further include one or more attachment points 129 for attachment of straps 1201 (FIG. 12) to secure the splint device 100, 200 onto a body area. It is envisioned that the straps 1201 may be of a hook and loop type. The number and placement of the attachment points 129 is a matter of discretion and may be varied as necessary for the desired task. Moreover, it is envisioned that ventilation holes or apertures (not shown) may be provided throughout each of the first and second members 101, 107 at any location.

Figure 4:
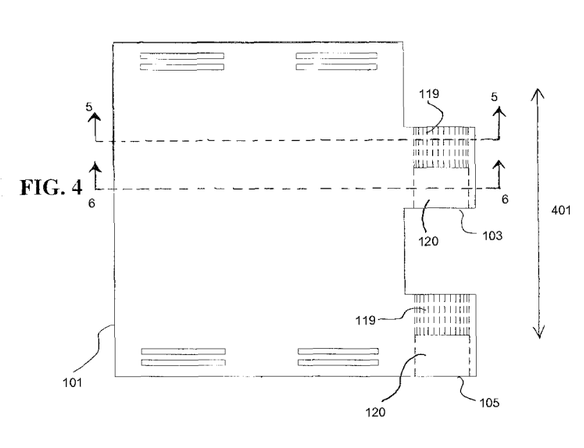
FIG. 4 is a front view of one embodiment of a first base member in accordance with the principles of the present disclosure.
Figure 5:
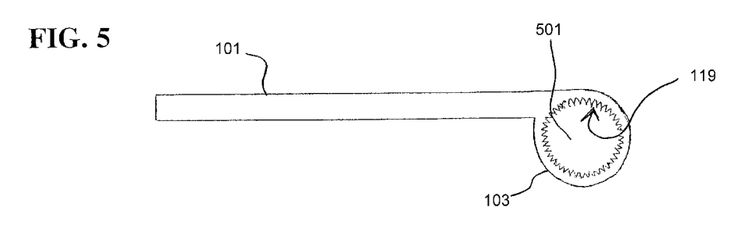
FIG. 5 is a cross-sectional view taken along lines 5-5 of FIG. 4.
Figure 6:
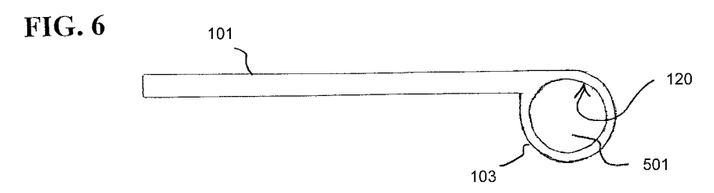
FIG. 6 is a cross-sectional view taken along line 6-6 of FIG. 4.

FIG. 4 is a front view of one embodiment of a first base member in accordance with the principles of the present disclosure, in which interior views of connector portions 103, 105, 109, 111 are provided for sake of clarity, while FIG. 5 is a cross-sectional view taken along lines 5-5 of FIG. 4, and FIG. 6 is a cross-sectional view taken along line 6-6 of FIG. 4.

Figure 7:
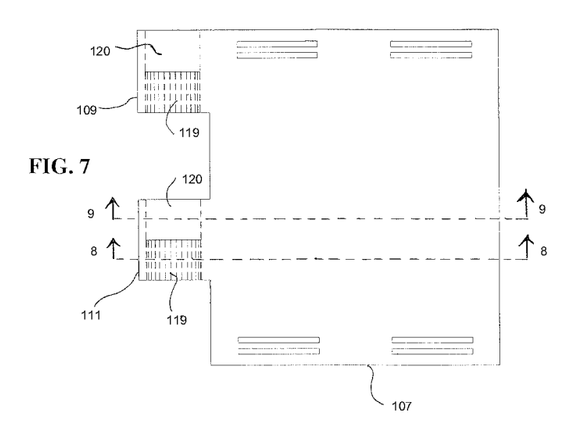
FIG. 7 is a front view of one embodiment of a second base member in accordance with the principles of the present disclosure.
Figure 8:
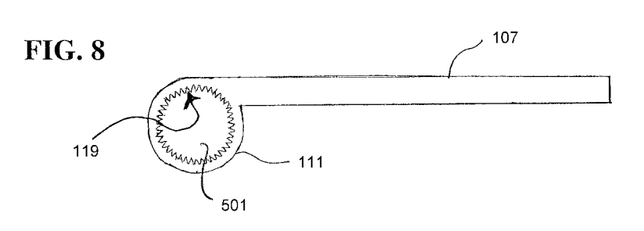
FIG. 8 is a cross-sectional view taken along lines 8-8 of FIG. 7.
Figure 9:
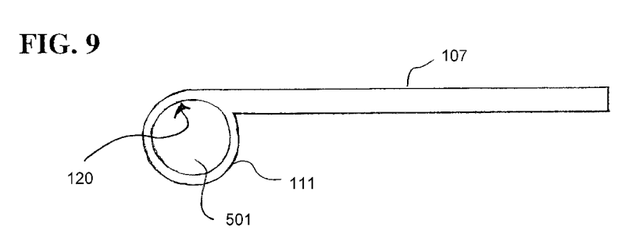
FIG. 9 is a cross-sectional view taken along lines 9-9 of FIG. 7.

Further, FIG. 7 is a front view of one embodiment of a second base member in accordance with the principles of the present disclosure, in which interior views of connector portions 103, 105, 109, 111 are provided for sake of clarity, while FIG. 8 is a cross-sectional view taken along lines 8-8 of FIG. 7 and FIG. 9 is a cross-sectional view taken along lines 9-9 of FIG. 7.

The first and second base members 101, 107 may each include first and second connector portions 103, 105 and 109, 111, respectively, which may comprise hollow cylindrically-shaped members each including a cavity 501 (FIGS. 5-6 and FIGS. 8-9) running substantially parallel to a length 401 (FIG. 4) of each of the first and second members 101, 107. Each of the first and second connector portions 103, 105, 109, 111 are affixed to their respective first and second members 101, 107 in a staggered fashion so that when the first and second members 101, 107 are aligned and joined, the connector portions 103, 105, 109, 111 fit together so that each cavity 501 forms a longitudinal passage 307 (FIG. 3) configured to receive a shaft 113 there through, which effectively provides a hinged connection between the first and second base members 101, 107.

The shaft 113 may comprise a cylindrically-shaped, rod-like member having a length which is engageable or with all of the connector portions 103, 105, 109, 111 when fully inserted therein. An exterior surface of the shaft 113 may include shaft coupling portions 117 and slidable shaft portions 125, each arranged in an alternating arrangement along a longitudinal direction of the shaft 113. For example, it is envisioned that the shaft coupling portions 117 may include coupling elements, which can axially engage with corresponding coupling elements of a base member 101, 107 (as described further below) to prevent the rotation of the shaft 113. It is envisioned that the slidable shaft portions 125 are devoid of coupling elements, for example, may comprise substantially smooth portions, and/or other surface configurations and features which do not axially engage with the coupling portions 119 of a base member 101, 107.

The shaft 113 may further include a shaft head 115 which in one embodiment has a width exceeding at least a width of the cavity of the connector portion 105 to prevent the shaft 113 from passing there through. Proximal to the head 115, a longitudinal groove 121 and first and second holes 124, 123 may be provided on the shaft 113, the function of which will be explained in more detail hereafter.

Shaft coupling elements 117 may comprise, e.g., a plurality of formations such as 'teeth,' grooves, splines, hooks, dimples, texturing, projections or the like disposed on the exterior surface of the shaft 113, and preferably arranged to enable movement of the shaft in a longitudinal direction, while preventing its rotational movement relative to the first and second connector portions 103, 105, 109, 111 when in a 'locked' position, as explained further below.

In one embodiment as shown, it is envisioned that a distal end portion and at least one medial portion comprise slidable shaft portions 125 which have no shaft coupling elements which would prevent rotation of the shaft 113. For example, the slidable shaft portions 125 may comprise a substantially smooth surface and/or comprise features which do not engage with connector coupling portions 119, as described further below.

It is envisioned that an interior surface of each of the first and second connector portions 103, 105, 109, 111 includes connector coupling portions 119 and slidable connector portions 120, which are provided in an alternating arrangement along a longitudinal direction 401 of the base members 101, 107. The connector coupling portions 119 may comprise coupling elements such as a plurality of formations such as 'teeth,' grooves, splines, hooks, dimples, texturing, projections or the like which are configured to be connectable and mateable with the shaft coupling elements 117, such that an axial engagement between the shaft 113 and connector portions 103, 105, 109, 111 can be achieved.

An exemplary arrangement of the slidable and coupling portions of the shaft 113 with respect to the coupling portions 103, 105, 109, 111 will now be described. According to one embodiment, a length of the end portion on the shaft 113 comprising a slidable shaft portion 125 is at least equal to a length 127 of the connector coupling portion 119 of the connector portion 109. Further, a length of a medial portion comprising a slidable shaft portion 125 is at least equal to a length 127 of the connector coupling portion 119 of the connector portion 111. The remaining areas of the surface of the shaft 113 include shaft coupling elements 117.

In the embodiments shown, the coupling portions 103, 105 on the first base member 101 may also include a similar alternating arrangement of the connector coupling portions 119 and slidable coupling portions 120, though in a reverse order as compared to the second base member 107. For example, each of the slidable shaft portions 125 may have a length at least equal to a length of the connector coupling portion 119 of the connector portions 103, 105. This enables the insertion of the shaft 113 through either side of the splint device 100, 200 and thus provides a splint device 100, 200 which may be used in a reverse configuration, for example, wherein the first base member 101 may be caused to be adjustable with respect to the shaft 113.

Figure 2:
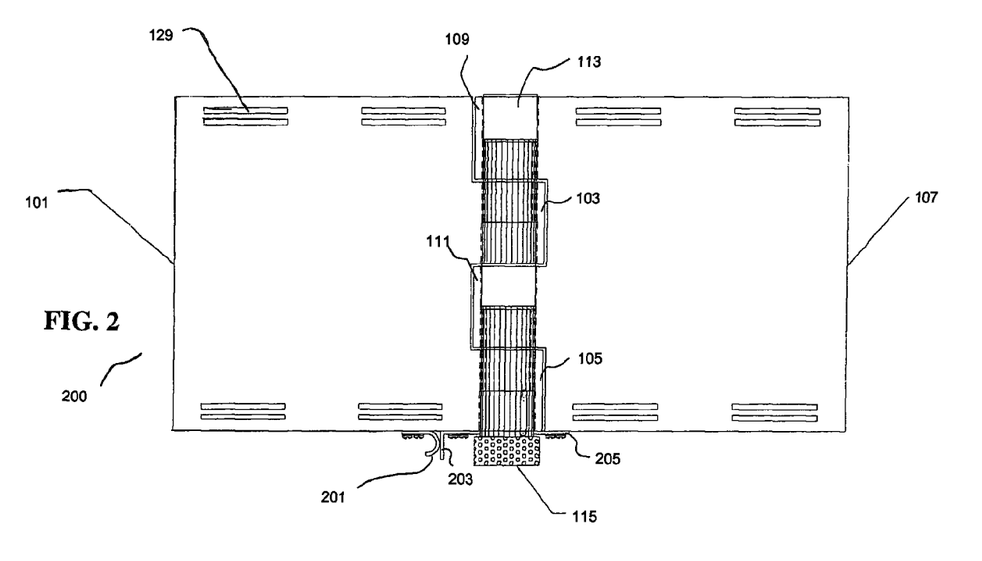
FIG. 2 is a front view of one embodiment of the components of a splint device in an assembled and locked position in accordance with the principles of the present disclosure.
Figure 3:
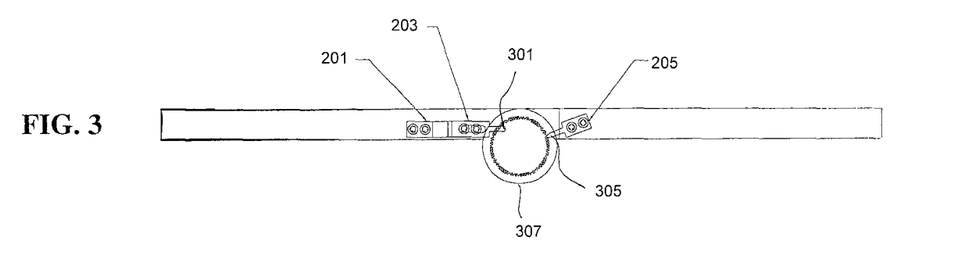
FIG. 3 is a bottom view of the components of the system shown in FIG. 2.

FIG. 2 is a front view of one embodiment of the components of a splint device in an assembled and locked position in accordance with the principles of the present disclosure, in which interior views of the shaft 113 and connector portions 103, 105, 109, 111 are provided for sake of clarity, while FIG. 3 is a bottom view of the components of the device of FIG. 2. To assemble the splint device, each of the first and second base members 101, 107 are joined to align their respective connector portions 103, 105, 109, 111 and form a single longitudinal passage 307, and a shaft 113 is inserted into and disposed within the longitudinal passage 307 until a lip of the shaft head 115 abuts the connector portion 105.

Once fully inserted through either end of the splint device 100, 200, the end portion which includes a slidable shaft portion 125, will align with the slidable connector portion 120, while the shaft coupling element 117 will be in contact with substantially all of the areas 127 of the second base connector 107. This results in axial engagement of the respective coupling elements 117, 119 and prevents rotation of the shaft 113 with respect to either of the base members 101, 107, thus providing the locked position.

Figure 10:
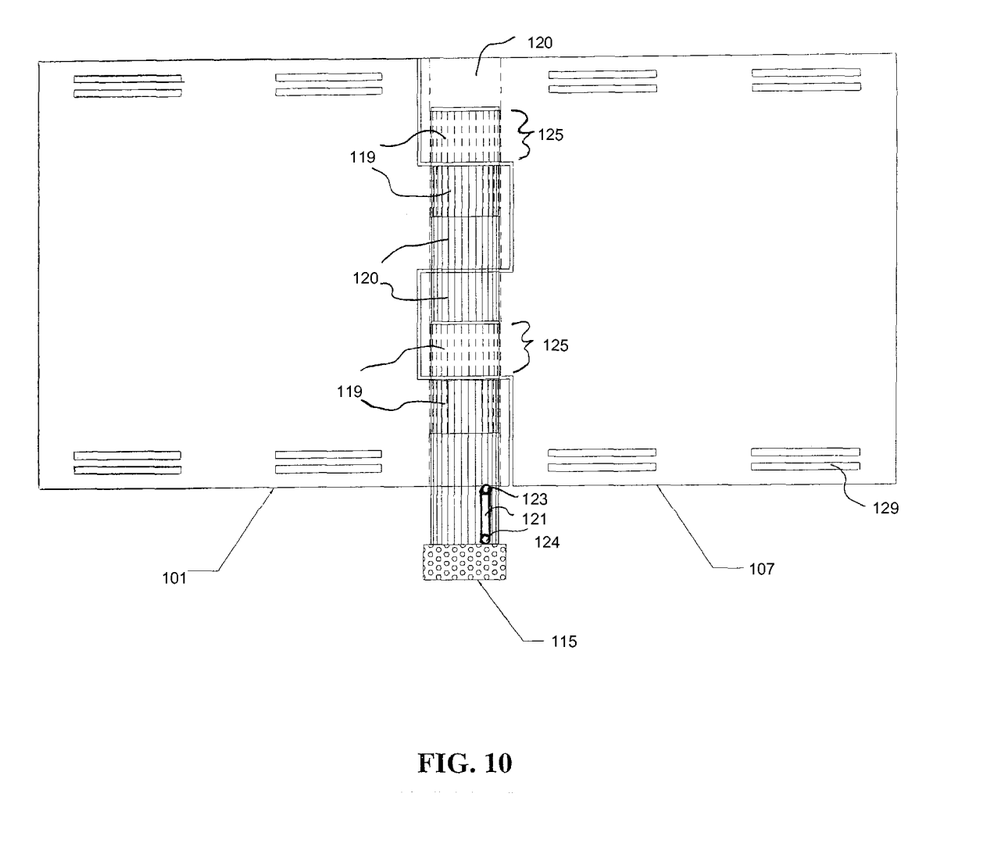
FIG. 10 is a front view of one embodiment of the components of a splint device in an assembled and adjustable position in accordance with the principles of the present disclosure.

In an exemplary embodiment, either end of one of the two base members may include a locking member 203 mounted proximate to the point of entry of the shaft 113 for enabling the shaft 113 to be contained within the cavities 501 while still permitting a limited range of longitudinal motion. It is envisioned that the locking member 203 may comprise a pin 301 receivable within and slidable along the groove 121 and separately insertable within the holes 124, 123. The shaft 113 may be inserted within the cavities 501 such that the groove 121 and first and second stop holes 124, 123 are oriented to enable insertion of the pin 301. A biasing member 201 may be provided adjacent to the locking member 203 to impart a force thereon to maintain the insertion of the pin 301 within either of the stop holes 124, 123. The biasing member 201 may comprise, e.g., a spring or other element which may impart continuous force onto the pin 301. Thus, the splint device 100, 200 may be maintained in either a locked position (as shown in FIG. 2) or an adjustable position (as shown in FIG. 10).

When the shaft 113 is fully inserted within the longitudinal passage 307 as shown in FIG. 2, the pin 301 may be insertable within the first stop hole 124, and maintained within the first hole 124 due to the biasing member 201. Thereafter, the shaft 113 may be partially pulled in an axial direction (as shown in FIG. 10) to provide a splint device in an adjustable position, but the shaft 113 has a limited axial range of motion and is thus prevented from being pulled out entirely due to the pin 301 being slid into and inserted into the second stop hole 123.

An alignment member 205 may be provided affixed to either of the base members 101, 107 and includes a clicker pin 305 configured to contact the shaft coupling elements 117. In one embodiment as shown in FIG. 2, the alignment member 205 is provided affixed to the second base member 107 (which is configured to be moveable relative to the shaft 113 when the splint device is in an adjustable position, as explained further below).

In operation, as discussed hereafter, it is envisioned that the clicker pin 305 of the alignment member 205 may be lightly dragged against the shaft coupling elements 117 during rotation of the second base member 107, so that the connector coupling portions 119 of the second base member 107 may be maintained in alignment with the shaft coupling portions 117 even during pivoting of the second base member 107, thus facilitating proper reinsertion of the shaft 113 into the cavity 501. In one embodiment, it is envisioned that the clicker pin 305 facilitates incremental adjustment of the second base member 107 with the first base member 101 while maintaining their proper alignment.

Each of the locking member 203, the biasing member 201 and alignment member 205 may be mounted with any connecting means, such as screws and the like. The locking member 203 may further include a slot (not shown) to allow the pin 301 to freely travel into and out of the holes 123, 124 and groove 121 in the shaft 113 without binding. FIG. 10 is a front view of one embodiment of the components of a splint device 100, 200 in an assembled and adjustable position in accordance with the principles of the present disclosure, in which interior views of the shaft 113 and connector portions 103, 105, 109, 111 are shown for sake of clarity.

In the 'adjustable position,' one of the base members 101, 107 may be moveable with respect to the other to allow adjustment of the angle of the splint (i.e., the angle of the base members 101, 107 with respect to each other). That is, one of the base members 101, 107 may be rendered a "movable base member." In the view presented in FIG. 10, it is noted that the groove 121 and holes 123, 125 are shown for sake of clarity, but in actual operation, the holes 123, 125 would be engaged with the locking member 203 and thus hidden from this front view.

To enable the splint device 100, 200 to be adjusted, the shaft 113 is pulled out in an axial direction to be partially removed from the cavity 501. Only partial removal of the shaft 113 from the cavity 501 is permitted however, due to the action of the locking member pin 301 being inserted into the second stop hole 123, which results in the shaft 113 being locked into the adjustable position. In one embodiment, it is envisioned that the shaft 113 is enabled to be pulled out to the extent in which its slidable portions 125 fully meet with and are oriented within the coupling portions 119 of the second base member 107, as explained further below.

Namely, once the shaft 113 is partially extended in an axial direction, each of the slidable regions 125 of the shaft 113 will be caused to coincide with each of the areas 127 on the second base member 107 having the connector coupling portions 119. Accordingly, this releases any axial engagement between coupling portions/elements 119 and 117 and the shaft 113 will be free to rotate with respect to the second base member 107. Thus, the second base member 107 will be able to be freely pivoted with respect to the shaft 113. It is envisioned that various angular adjustments and orientations of the second base member 107 with respect to the first base member 101 may thus advantageously be easily achieved.

Once a desired angle of the base members 101, 107 of the splint device is achieved, the shaft 113 may be pushed axially back into the cavity 501, thus reengaging the shaft coupling elements 117 with the connector coupling portions 119 and preventing further pivotal movement of the first and second base members 101, 107 with respect to each other.

Accordingly, a splint device is provided having base members for contacting a body region which are easily angularly adjustable and enable quick adjustment to secure and immobilize the body region in a desired position.

In assembly, operation and use, a splint device 100, 200, similar to the systems described above, can be employed with a surgical procedure, such as for a correction treatment of a limb. It is contemplated that one or all of the components of splint device 100, 200 can be delivered or implanted as a pre-assembled device or can be assembled in situ. Splint device 100, 200 may be completely or partially revised, removed or replaced. It is further contemplated that the components of a splint device 100, 200 and method of use may be used to prevent or minimize joint, bone or soft tissue damage in individuals of various ages.

Figure 12:
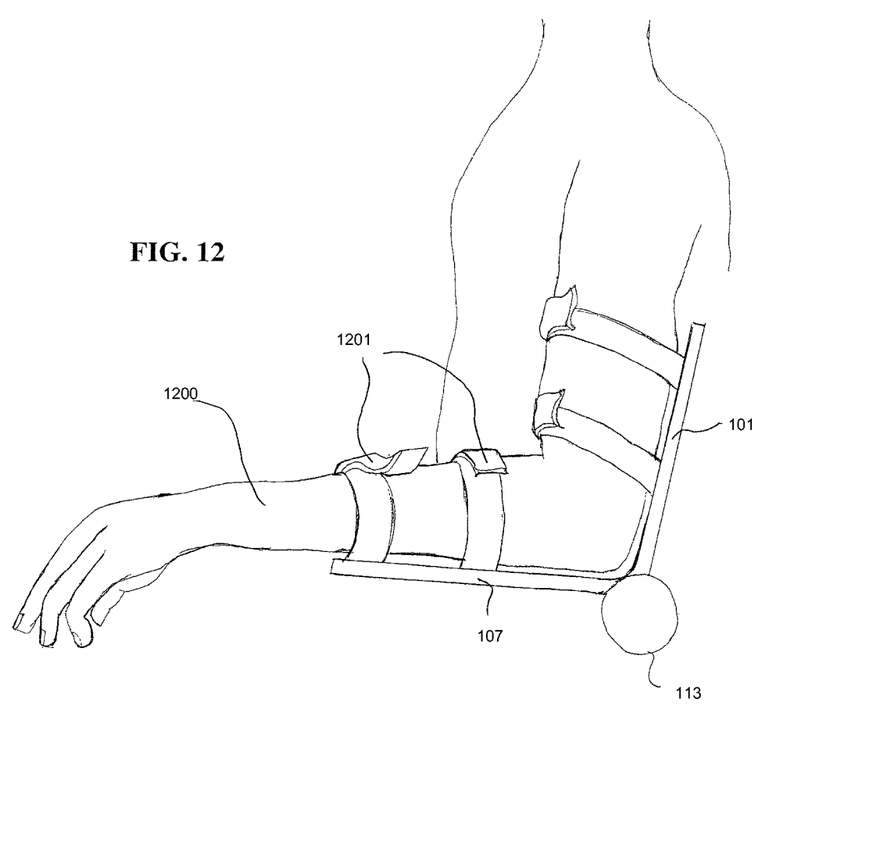
FIG. 12 is a side elevation view of a splint device accordance with principles of the present disclosure shown supporting the upper arm and forearm of a patient.

For example, as shown in FIG. 12, a splint device 200, described above, can be employed to support and immobilize a body region, such as an arm 1200. FIG. 12 is a side elevation view of a splint device accordance with principles of the present disclosure shown supporting the upper arm and forearm of a patient. However, it is envisioned that a splint device according to the present disclosure may be employed with or adapted to support and immobilize any area or region of the body.

In one embodiment, splint device 100, 200 may be employed in conjunction with an agent, which may be disposed, packed or layered within, on or about the components and/or surfaces of splint device 100, 200. It is envisioned that the agent may include bone growth promoting material.

If surgery is needed to set a bone, it is contemplated that an agent may be employed to aid in healing. The agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of splint device 100, 200 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It is envisioned that the use of microsurgical and image guided technologies may be employed to access, view and repair tissue damage, with the aid of splint device 100, 200. Upon completion of the procedure, the surgical instruments and assemblies are removed and the incision is closed.

To use a splint device according to the present disclosure to immobilize an arm 1200, a medical practitioner may be provided with access to an area of the body desired to be immobilized, and with the first and second base members 101, 107 hingedly connected via a shaft 113. The practitioner can adjust the shaft member 113 by pulling on the shaft 113 to partially remove it from the longitudinal passage 307 until axial engagement of the shaft 113 with respect to the second base member 107 is released, thus causing the splint device to assume an unlocked or adjustable position in which the second base member 107 is freely pivotable with respect to the shaft 113 (i.e., is caused to become a movable base member).

The movable base member 107 is pivoted open as necessary to increase the angle of the first and second base members 101, 107 to contact the upper arm and forearm areas of the arm 1200 so as to support either side of the elbow joint. Once the base members 101, 107 are placed on the arm 1200, straps 1201 may be secured to the upper and lower arm to secure each base member 101, 107 to the upper arm and forearm areas. The movable base member may be further pivoted to close the angle of the first and second base members 101, 107 to support the arm at a desired angle and position.

Once the desired angle of the first and second base members 101, 107 is obtained, the shaft 113 may be adjusted by pushing it back into the longitudinal passage 307 to cause axial engagement of the shaft 113 with respect to the second base member 107. This enables the position of the base members 101, 107 to be fixed relative to each other, thus locking the splint device and immobilizing the arm 1200.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A splint system comprising:
   a first base member including at least one connector portion having a cavity, wherein an interior surface of the cavity includes coupling portions;
   a second base member forming a hinged connection with the first base member, each of the first and second base members including at least one surface for contacting a body region, the second base member including at least one connector portion having a cavity, wherein an interior surface of the cavity includes slidable portions and coupling portions, and wherein the first and second base members are aligned so that each cavity of their respective at least one connector portions form a longitudinal passage; and
   a shaft member disposed in said longitudinal passage, wherein a surface of the shaft member includes slidable portions and coupling portions alternating along a longitudinal direction of the shaft member, such that when the slidable portions of the shaft member align with the coupling portions of the second base member, the first and second base members are angularly adjustable, and when the coupling portions of the shaft member align with the coupling portions of the second base member, the first and second base members are fixed relative to each other.

2. The system of claim 1, wherein the slidable portions comprise substantially smooth portions and the coupling portions include surface projections.

3. The system of claim 1, wherein the coupling portions of the shaft member are configured to be mateable with the coupling portions of the second base member.

4. The system of claim 3, wherein the coupling portions of the shaft member are mated with the coupling portions of the first and second base member to provide axial engagement of the shaft member with respect to the first and second base member.

5. The system of claim 1, wherein the slidable and coupling portions on the second base member are provided in an alternating arrangement along a longitudinal direction of the second base member.

6. The system of claim 1, wherein the shaft is fully insertable within the longitudinal passage to provide a locked position in which the coupling portions of the shaft member align with the coupling portions of the second base member.

7. The system of claim 6, wherein the locked position is provided by axial engagement of the shaft member with respect to the first and second base members.

8. The system of claim 1, wherein the shaft is configured to be partially removable from the longitudinal passage to provide an adjustable position.

9. The system of claim 8, wherein the adjustable position is provided by orienting the slidable portions of the shaft member within the coupling portions of the second base member to enable pivotal movement of the second base member relative to the shaft member.

10. The system of claim 1, further comprising a locking member for maintaining the splint device in a locked position.

11. The system of claim 10, wherein the shaft member includes a longitudinal groove having first and second stop holes.

12. The system of claim 11, wherein the locking member includes a pin configured to be received within said groove and inserted within the first stop hole to maintain the shaft member in the locked position.

13. The system of claim 11, wherein the pin is configured to be inserted within the second stop hole to maintain an adjustable position of the splint device.

14. The system of claim 1, wherein each of the first and second base members includes at least one attachment point.

15. The system of claim 1, wherein the first base member further includes slidable portions.

16. The system of claim 13, wherein the slidable and coupling portions on the first base member are provided in an alternating arrangement along a longitudinal direction of the first base member.

17. The system of claim 1, further comprising an alignment member affixed to the second base member for maintaining the alignment of the coupling portions of the second base member with the coupling portions of the shaft member during adjustment of the second base member.

18. The system of claim 17, wherein the adjustment of the base member comprises pivotal movement of the second base member with respect to the shaft member when the splint device is in an adjustable position.

19. A splint system comprising:
a first base member including two connector portions having a cylindrical cavity, wherein an interior surface of the cylindrical cavity includes slidable portions and coupling portions in an alternating arrangement along a longitudinal direction of the first base member;
a second base member including two connector portions having a cylindrical cavity, wherein an interior surface of the cylindrical cavity includes slidable portions and coupling portions in an alternating arrangement along a longitudinal direction of the first base member, and wherein the first and second base members are aligned so that each cylindrical cavity of their respective two connector portions form a longitudinal passage; and
a shaft member inserted into said longitudinal passage, wherein a surface of the shaft member includes slidable portions and coupling portions in an alternating arrangement along a longitudinal direction of the shaft member, wherein the shaft is fully insertable within the longitudinal passage to provide a locked position in which the coupling portions of the shaft member are engaged with the coupling portions of the first and second base members to fix a position of the first member relative to the second member, and wherein the shaft is configured to be partially removable from the longitudinal passage to provide an adjustable position in which the slidable portions of the shaft member are oriented within the coupling portions of the second base member to enable pivotal movement of the second base member relative to the shaft member.

20. A method for immobilizing an area of the body, the method comprising the steps of:
accessing an area of the body desired to be immobilized;
providing a first base member including at least one connector portion having a cavity, wherein an interior surface of the cavity includes coupling portions, a second base member including at least one connector portion having a cavity, wherein an interior surface of the cavity includes slidable and coupling portions, and wherein the first and second base members are aligned so that each cavity of their respective at least one connector portions form a longitudinal passage, and a shaft member inserted into said longitudinal passage, wherein a surface of the shaft member includes slidable and coupling portions;
adjusting the shaft member to an adjustable position and placing the first and second base members on the area of the body;
pivoting at least one of the base members to a desired position; and
adjusting the shaft member to a locked position to immobilize the area of the body by fixing the position of the first member relative to the second member.

* * * * *